United States Patent [19]
Machek et al.

[11] Patent Number: 6,002,969
[45] Date of Patent: Dec. 14, 1999

[54] CARDIAC LEAD WITH SHAPE-MEMORY STRUCTURE

[75] Inventors: James E. Machek; Paul R. Spehr; Edward A. Schroeppel, all of Lake Jackson, Tex.

[73] Assignee: Intermedics Inc., Angleton, Tex.

[21] Appl. No.: 09/129,400

[22] Filed: Aug. 5, 1998

[51] Int. Cl.[6] .................................................. A61N 1/05
[52] U.S. Cl. ........................................................ 607/122
[58] Field of Search ................................. 607/122, 123, 607/119, 132

[56] References Cited

U.S. PATENT DOCUMENTS

| | | | |
|---|---|---|---|
| 4,516,584 | 5/1985 | Garcia | 128/785 |
| 4,820,298 | 4/1989 | Leveen et al. | 623/1 |
| 4,950,258 | 8/1990 | Kawai et al. | 604/281 |
| 5,049,591 | 9/1991 | Hayashi et al. | 521/159 |
| 5,108,417 | 4/1992 | Sawyer | 606/198 |
| 5,128,197 | 7/1992 | Kobayashi et al. | 428/225 |
| 5,129,404 | 7/1992 | Spehr et al. | 128/785 |
| 5,129,405 | 7/1992 | Milijasevic et al. | 128/785 |
| 5,189,110 | 2/1993 | Ikematu et al. | 525/314 |
| 5,273,053 | 12/1993 | Pohndorf | 607/132 |
| 5,545,204 | 8/1996 | Cammilli et al. | 607/123 |
| 5,575,766 | 11/1996 | Swartz et al. | 604/53 |
| 5,617,854 | 4/1997 | Munsif | 128/642 |
| 5,632,734 | 5/1997 | Galel et al. | 604/282 |
| 5,634,936 | 6/1997 | Linden et al. | 606/213 |

OTHER PUBLICATIONS

C. Liang et al.; Preliminary Investigation of Shape Memory Polymers and Their Hybrid Composites; Smart Structures and Materials ASME, AD–vol. 24/AMD–vol. 123; pp. 97–105; 1991.

Paul Frenger; Biomedical Uses of Shape Memory Polymers; Biomedical Sciences Instrumentation, vol. 29; pp. 47–50; 1993.

N. Koczera et al.; Shape Memory Polymers For Surgical Staples, Proceedings of the 12th Southern Biomedical Engineering Conference in New Orleans, IEEE; pp. 60–62; 1993.

Manas Chanda et al.; Plastics Technology Handbook, Plastics Technology Handbook, Chapter 6; pp. 721–723; 1993.

S. Hayashi et al.; Properties and Applications of Polyurethane–Series Shape Memory Polymer, ANTEC '94; pp. 1998–2001; 1994.

Shunichi Hayashi et al.; Room–Temperature–Functional Shape–Memory Polymers, Plastics Engineering; pp. 29–31; Feb. '95.

V. Tucci et al.; Shape Memory Polymers For External Fracture Fixation, ANTEC '95; pp. 2102–2104; 1995.

Robert R. Brownlee et al.; Toward Optimizing a Preshaped Catheter and System Parameters to Achieve Single Lead DDD Pacing, PACE, vol. 20; pp. 1354–1358; May 1997.

*Primary Examiner*—Scott M. Getzow
*Attorney, Agent, or Firm*—Schwegman, Lundberg, Woessner and Kluth

[57] ABSTRACT

A cardiac stimulator lead is provided that includes a lead body that has a connector for coupling to a cardiac stimulator and a flexible insulating sleeve that has a first outer diameter. An electrode is coupled to the insulating sleeve. A conductor wire is coupled between the connector and the electrode. An annular seat is coupled to the lead body and is composed of a thermally-sensitive shape-memory polymeric material whereby the seal is deformable in situ from a temporary shape with a second outer diameter to a permanent shape with a third outer diameter that is greater than the second outer diameter. A shape-memory polymeric suture sleeve may be included that can tightly clamp the lead sleeve in situ.

18 Claims, 6 Drawing Sheets

CARDIAC LEAD WITH SHAPE-MEMORY STRUCTURE

BACKGROUND OF THE INVENTION

1. Field of the Invention

This invention relates generally to cardiac stimulator leads, and more particularly to a cardiac stimulator lead that includes a lead body with a shape-memory polymeric annular seal and a shape-memory polymeric suture sleeve.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. Most such leads include an elongated flexible tubular, electrically insulating sleeve that is connected proximally to a connector that is adapted to couple to the header of the cardiac stimulator can, and distally to a tip electrode that is positioned near the tissue requiring stimulation. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac stimulator and the incision is closed. The implantation route and site are usually imaged in real time by fluoroscopy to confirm proper manipulation and placement of the lead.

Prior to closure, a suture sleeve (if not already in place) is slipped over the lead sleeve, positioned proximal to the site of transvenous entry, and sutured in place to body tissue. The suture sleeve is designed to anchor a portion of the lead to a preselected portion of tissue proximal to the site of transvenous entry and to restrict the longitudinal movement of the lead following implantation. The design goal is not to eliminate all longitudinal movement of the lead since some longitudinal movement thereof is inevitable due to normal chest and heart movements and to physical exertion. Rather, the aim is to prevent radical longitudinal movements of the lead that could dislodge the tip electrode from the endocardium or even fracture the conductor wires inside the lead. The movement restricting function of conventional suture sleeves is accomplished by tying one or more ligature sutures around the suture sleeve that clamp the suture sleeve to the exterior of the lead sleeve.

One difficulty associated with conventional suture sleeve design is the potential for stress risers created by the ligature sutures that clamp the suture sleeve to the lead sleeve. The crimping action of a ligature suture is spread over a very small area. Thus, the ligature point can act as a fulcrum for bending movement of the wires inside the lead sleeve. Fatigue failure of the wires can result. If the suture is tied too tightly, metal fatigue may be accelerated or worse, the wires may be damaged at the time of implantation. While a skilled physician can often avoid overtightening, there remains the residual problem of a large crimping force applied to a very small area.

In addition to irregular stresses imparted on the lead, conventional suture sleeves are susceptible to becoming unclamped from the lead sleeve. The problems stems from the gradual loosening of the ligature sutures over time. A suture may loosen due to a variety of causes, such as improper suturing by the physician, stretching of the suture material, heavy exertion by the patient or other causes. Regardless of the particular origin, an unclamped suture sleeve can no longer prevent the implanted lead from making large longitudinal movements. Such unchecked movements may result in the tip electrode detaching from the endocardium.

As noted above, the lead must be connected to the cardiac stimulator prior to closure. This entails inserting the connector into a passage in the header of the cardiac stimulator and manipulating some type of anchoring mechanism, such as a set screw, to hold the connector in place. Most conventional connectors include one or more external O-rings to provide a seal against the penetration of body fluids into the passage after implantation. Like many types of O-rings used as fluid seals in other industrial applications, conventional connector O-rings are molded with a circular or elliptical profile and an outer diameter based on an anticipated inner diameter of the header passage. The outer diameter of the O-ring is chosen to be slightly larger than the inner diameter of the passage. When the connector is pushed into the passage, the O-rings elastically deform to conform to the passage. Some effort is normally required to insert the connector even where the dimensions of the O-rings and the passage are closely matched.

Difficulties arise with conventional connector O-rings where the dimensions of the O-rings, the header passage, or both fall outside manufacturing tolerances. Where the O-rings are too large in relation to the passage, insertion may be difficult and require force that may ultimately damage the O-rings. Where the O-rings are too small in relation to the passage, an inadequate seal may be formed. Because of the rather small dimensions involved, even a small imperfection in the seal of the O-ring is often amplified due to capillary action.

The present invention is directed to overcoming or reducing the effects of one or more of the foregoing disadvantages.

SUMMARY OF THE INVENTION

In accordance with one aspect of the present invention, a cardiac stimulator lead is provided. The cardiac stimulator lead includes a lead body that has a connector for coupling to a cardiac stimulator and a flexible insulating sleeve that has a first outer diameter. An electrode is coupled to the insulating sleeve. A conductor wire is coupled between the connector and the electrode. An annular seal is coupled to the lead body and is composed of a thermally-sensitive shape-memory polymeric material whereby the seal is deformable in situ from a temporary shape with a second outer diameter to a permanent shape with a third outer diameter that is greater than the second outer diameter.

In accordance with another aspect of the present invention, a suture sleeve for a cardiac lead that has an insulating sleeve with a first outer diameter is provided. The suture sleeve includes a tubular body that has a lumen extending therethrough whereby the tubular body may be slipped over the cardiac lead. The tubular body is composed of a thermally-sensitive shape-memory polymeric material whereby the tubular body is deformable in situ from a temporary shape with a first inner diameter to a permanent shape with a second inner diameter that is less than the first inner diameter and the first outer diameter of the insulating sleeve.

In accordance with another aspect of the present invention, a cardiac stimulator lead is provided. The cardiac stimulator lead includes a tubular lead body that has a connector for connecting to a cardiac stimulator and an insulating sleeve coupled to the connector that has a first outer diameter. An electrode is coupled to the insulating sleeve. A conductor wire is coupled between the connector and the electrode. A suture sleeve is included that has a lumen extending therethrough to receive the insulating sleeve. The suture sleeve is composed of a thermally-sensitive shape-memory polymeric material whereby the suture sleeve is deformable in situ from a temporary shape with a first inner diameter to a permanent shape with a second inner diameter that is less than the first inner diameter and the first outer diameter of the insulating sleeve.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
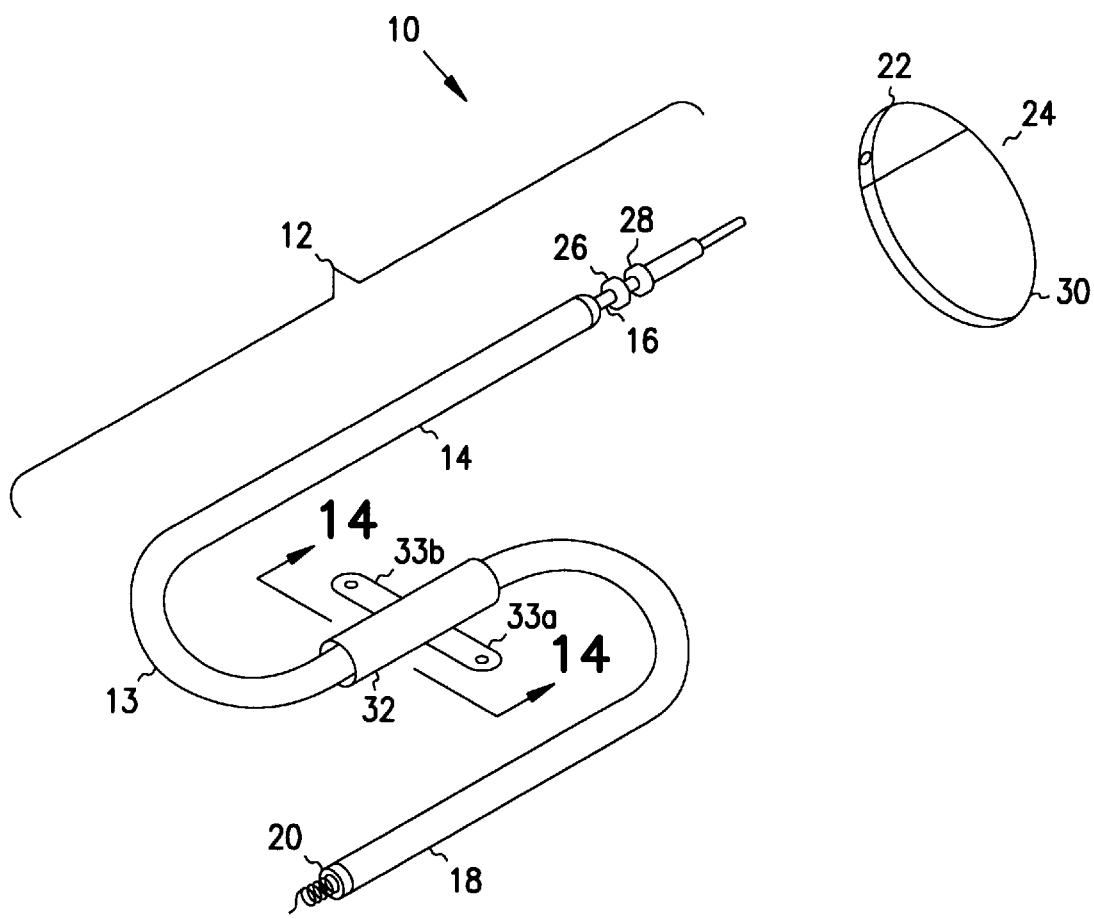
FIG. 1 is a pictorial view of an exemplary embodiment of a cardiac stimulator lead and a cardiac stimulator in accordance with the present invention.

In the drawings described below, reference numerals are generally repeated where identical elements appear in more than one figure. Turning now to the drawings, and in particular to FIG. 1, there is shown an exemplary embodiment of a cardiac stimulator lead 10. The lead 10 includes a lead body 12 that has a flexible insulating sleeve 13 with a proximal end 14 coupled to a connector 16, and a distal end 18 coupled to a tip electrode 20. The connector 16 is designed to be inserted into the header 22 of a cardiac stimulator 24 at the time of implantation. Note that the lead body 12 is shown highly exaggerated in size relative to the cardiac stimulator 22. To prevent the intrusion of body fluids into the header 22 following implantation, the lead body 12 is provided with two annular seals or O-rings 26 and 28.

The cardiac stimulator 24 includes the aforementioned header 22 coupled to a can or housing 30. The can 30 encloses various circuitry to transmit signals to and from the lead 10. Depending upon the particular circuitry implemented in the can 30, the cardiac stimulator 24 may function as a pacemaker, a cardioverter/defibrillator, or other type of stimulator or a sensing instrument.

A suture sleeve 32 is positioned around the sleeve 13 and is provided with suture wings 33a and 33b. During implantation, the suture sleeve 32 is sewn to body tissue at the site of transvenous entry by suturing the suture wings 33a and 33b to tissue. As discussed more below, the suture sleeve 32 is a tubular member that may be composed of a thermally-sensitive shape memory polymeric material that is deformable in situ to provide a tight engagement between the suture sleeve 32 and the lead sleeve 13.

The sleeve 13 is a flexible tubular member that provides a robust, electrically insulating coupling between the connector 16 and the electrode 20. The sleeve 13 protects one or more fine gage conductor wires enclosed therein from body fluids and tissues, and is advantageously composed of a biocompatible, electrically insulating material, such as silicone, polyurethane, or like materials.

Figure 2:
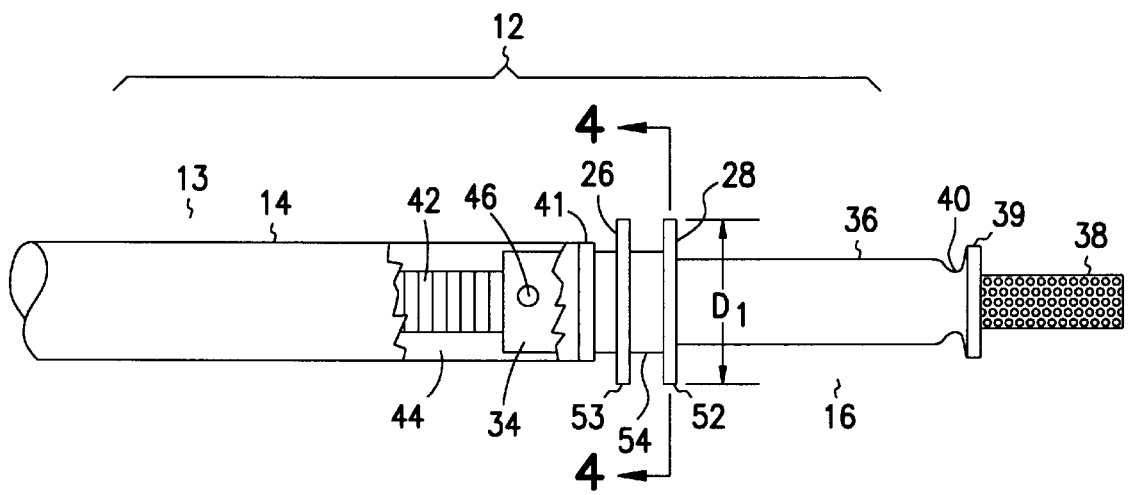
FIG. 2 is a detailed side view of the lead connector portion of the cardiac stimulator lead shown in FIG. 1.

The detailed structure of the connector 16 and the annular seals 26 and 28 may be understood by referring now to FIG. 2, which is a magnified side view of the connector 16 and the proximal end 14 of the lead sleeve 13. The connector 16 includes a generally tubular conducting chassis 34 that is covered by an insulating jacket 36. The proximal end of the chassis 34 is not covered by the jacket 36 and terminates in a conductor pin 38 that serves to establish electrical contact with a corresponding contact in the header 22 shown in FIG. 1. The chassis 34 may be composed of a variety of biocompatible conducting materials, such as titanium, MP35N alloy, stainless steel, or like materials. The insulating jacket 36 may be composed of a variety of biocompatible insulating materials, such as silicone, polyurethane, or like materials. The proximal end of the jacket 36 defines an O-ring 39 that tapers down distally to form a groove 40. The distal end of the insulating jacket 36 includes an annular rim 41 against which the end of the proximal end 14 of the lead sleeve 13 is abutted. The proximal end 14 is secured to the connector 16, and more specifically to the chassis 34, by application of a suitable biocompatible medical grade adhesive, such as a silicone adhesive or any of a variety of biocompatible two stage adhesives. A portion of the proximal end 14 has been peeled away to reveal a conductor wire 42 disposed in the lumen 44 of the lead sleeve 13. The conductor wire 42 is connected proximally to the chassis 34 at the point designated 46, and distally to the tip electrode 20 shown in FIG. 1. The area designated 46 in FIG. 2 consists generally of a circular opening in the chassis through which an end of the conductor wire 42 is projected and laser or spot welded.

Figure 3:
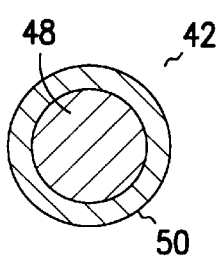
FIG. 3 is a cross-sectional view of the conductor wire that is jacketed with an insulating coating and enclosed within the lead shown in FIG. 1.

The detailed structure of the conductor wire 42 may be understood by referring now also to FIG. 3, which is a cross-sectional view of the wire 42. As shown in FIG. 3, the conductor wire 42 includes a conductor 48 that is individually jacketed by an insulating jacket 50. The conductor 48 may be composed of a variety of biocompatible conducting materials, such as titanium, MP35N alloy, stainless steel, drawn brazed strand of MP35N and silver, drawn filled tube of MP35N and a silver core, or like materials. The insulating jacket 50 may be composed of a variety of biocompatible conducting materials suitable for jacketing conductor wires, such as ETFE (fluoropolymer resin), or like materials. Alternatively, the conductor wire 42 may not be individually insulated, but may instead rely upon the lead sleeve 13 for electrical isolation from body fluids. The illustrated embodiment of the lead 10 is unipolar. However, the skilled artisan will appreciate that multi-polar arrangements are possible as well.

Figure 4:
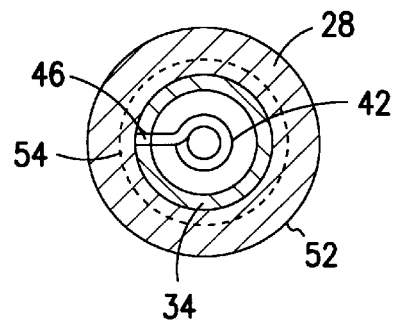
FIG. 4 is a cross-sectional view of FIG. 2 taken at section 4—4.
Figure 5:
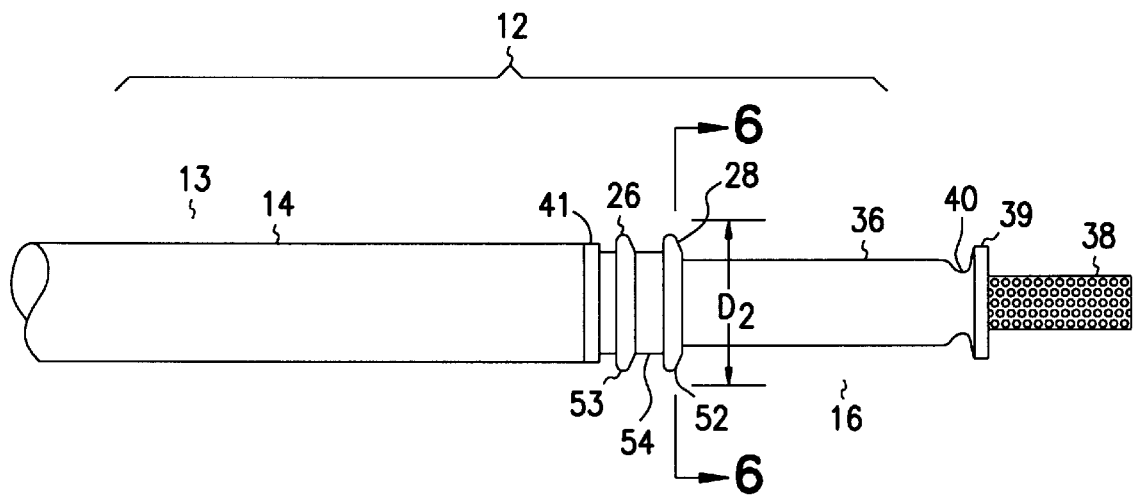
FIG. 5 is a detailed side view like FIG. 2 showing two annular seals deformed to a temporary shape prior to implantation of the lead in accordance with the present invention.

The detailed structure of the annular seals 26 and 28 may be understood by referring now to FIG. 2, to FIG. 4, which is a cross-sectional view of FIG. 2 taken at section 4—4, and to FIG. 5, which is a side view like FIG. 2. The following description of the annular seal 28 will be illustrative of the structure and function of the annular seal 26 as well. As shown in FIG. 4, the annular seal 28 is a disk-like member that is integrally molded with the insulating jacket 36 of the connector 16. The annular seal 28 includes an outer rim 52 that has a slightly rounded profile not unlike conventional toroid shaped O-rings. The seal 26 has an identical rim 53. Note that FIG. 4 shows the segment 54 of the insulating jacket 36 positioned between the annular seals 26 and 28 is shown in phantom, and the connection between the conductor wire 42 and the electrode 34 at the point designated 46 end-on.

Figure 6:
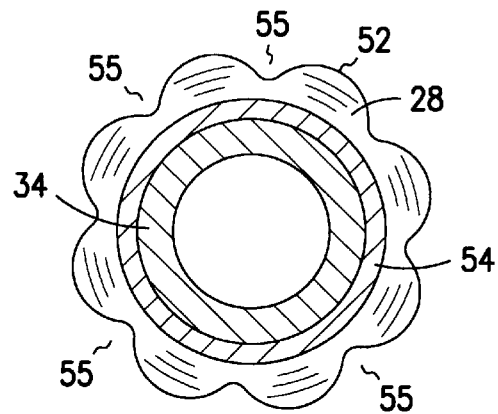
FIG. 6 is a cross-sectional view of FIG. 5 taken at section 6—6.

The annular seals 26 and 28 are advantageously composed of a thermally sensitive shape memory polymeric material. The shape-memory quality of the polymeric material enables the seals 26 and 28 to deform from a temporary shape to a permanent shape in response to thermal stimulation. In FIG. 2, the seals 26 and 28 are depicted in their permanent shapes with an outer diameter, $D_1$. FIG. 5 shows the seals 26 and 28 deformed into temporary shapes where each has an outer diameter, $D_2$, and where $D_2 < D_1$. The temporary shapes are established by folding the outer rims 52 and 53 of the seals 26 and 28 toward the jacket 36 so that the seals 26 and 28 take on a cup-like profile. FIG. 6 is a cross-sectional view of FIG. 5 taken at section 6—6 and shows a detailed end view of the deformation of the seal 28. Note that folding back of the seal 28 establishes a series of folds 55 therein.

The aforementioned heat-sensitive shape-memory polymeric material behaves generally like a rigid material while at temperatures below the glass transition temperature $T_g$, but undergoes significant softening and may be readily plastically deformed when heated above $T_g$. When the material is then cooled below $T_g$, the deformation is fixed and the shape remains stable. However, the original shape of the material may be recovered by reheating the material above $T_g$.

During production, the seals 26 and 28 are first molded into the permanent shapes shown in FIG. 2. A variety of well known molding techniques may be used to create the jacket 36 and the seals 26 and 28, such as injection molding, extrusion molding, or like techniques. The molding process subjects the heat-sensitive shape-memory polymeric material to a temperature well in excess of the $T_g$ for the material for a sufficient time to form the seals 26 and 28 into the permanent shapes. Thereafter, the seals 26 and 28 may be deformed into the temporary shapes shown in FIG. 2 by deforming the seals 26 and 28 at a temperature above $T_g$, and maintaining the seals 26 and 28 in the temporary shape while the temperature is lowered below $T_g$. After cooling below $T_g$, the seals 26 and 28 retain the temporary shape. However, if the seals 26 and 28 are later heated above $T_g$, they will deform substantially back into the permanent shapes in which they were originally molded. In this way, the seals 26 and 28 may be initially produced with a permanent shape that will establish a good fluid seal in the header 22 (see FIG. 1) but subsequently deformed into a temporary shape that will enable ready insertion of the connector 16 into the header 22 of the cardiac stimulator 24 shown in FIG. 1.

Where molding of the desired permanent shape is difficult in view of the molding process used and the small dimensions of the seals 26 and 28, the seals 26 and 28 may be molded with a first permanent shape that best suits the molding process. This may be, for example, a shape with a larger than desired permanent diameter. Thereafter, the seals 26 and 28 may be provided with a new permanent shape by heating the seals 26 and 28 above $T_g$, deforming the seals 26 and 28 into a new desired permanent shape, (e.g. a shape with a more suitable permanent diameter) and maintaining the seals 26 and 28 in that shape and at that temperature for a selected period of time. The heating time required to set the new permanent shape will depend on the particular polymer.

The materials selected for the seals 26 and 28 should have glass transition temperatures that are above the anticipated maximum body temperature so that they do not soften and deform into undesirable shapes after implantation. Normal body temperature usually falls within the range 36 to 37° C. However, a body subjected to high fever may reach about 42° C., so a $T_g \geq 42°$ C. should ensure that the deforming structures do not undergo undesirable deformation after implantation.

For long-term implantation, the seals 26 and 28 may be fabricated from heat-sensitive shape-memory polymeric material, such as polynorbornene supplied by Nippon Zeon of Japan, polyurethane supplied by Mitsubishi Heavy Industries of Japan, Calo.Mer™ supplied by Polymer Technology Group of California, or similar materials. If the lead 10 is designed for more transient implantation, materials such as polyvinyl chloride, or similar materials may be used in addition to the above-described materials.

The phrase "composed of" is used herein to describe the composition of a structure incorporating shape-memory characteristics and is intended to mean composed entirely of a thermally-sensitive shape-memory polymeric material or a mixture of a thermally-sensitive shape-memory polymeric material and a non-shape memory material. For example, the annular seals 26 and 28 may be composed of a mixture of a polynorbornene combined with polyurethane. Various combinations of thermally sensitive shape memory polymeric materials and non-shape memory polymeric materials may be used so long as the thermally sensitive shape memory characteristics and adequate elasticity of the annular seals 26 and 28 are retained.

Figure 7:
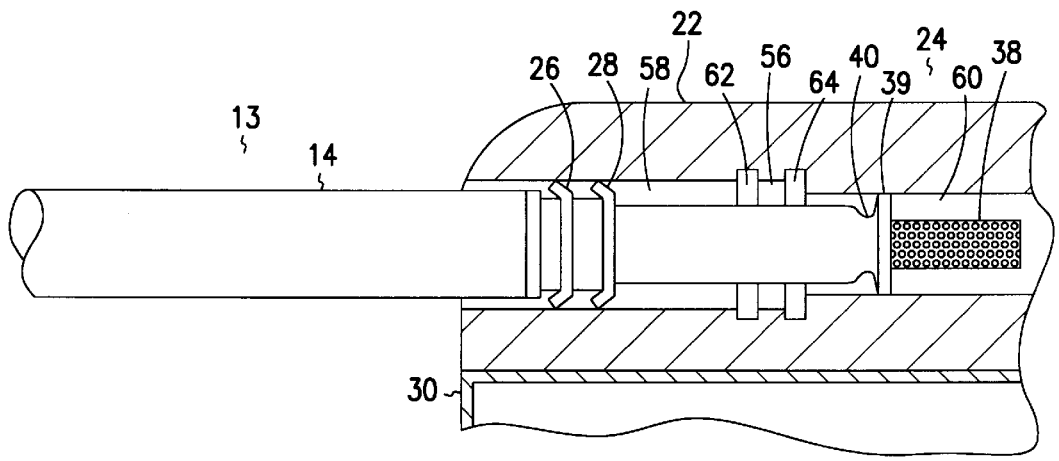
FIG. 7 is a detailed side view of the lead connector portion of the lead during insertion of the lead connector into the cardiac stimulator shown in FIG. 1 in accordance with the present invention.
Figure 8:
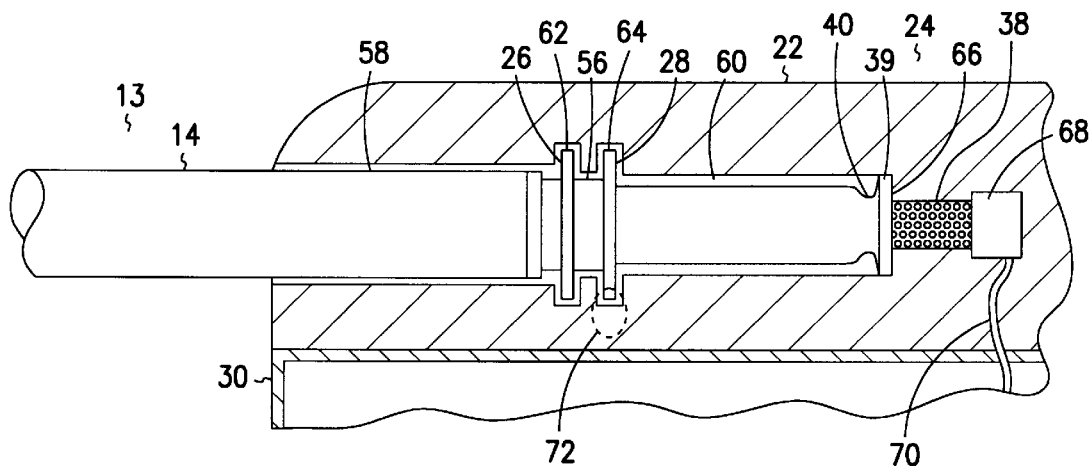
FIG. 8 is a detailed side view like FIG. 7 showing the lead fully connected to the cardiac stimulator shown in FIG. 1 in accordance with the present invention.

The connection of the lead connector 16 to the header 22 of the cardiac stimulator 24 may be understood by referring now to FIGS. 7 and 8, which are, respectively, cross-sectional views of a portion of the header 22 and the cardiac stimulator can 30 with the lead connector 16 partially inserted and fully inserted therein. The header 22 includes a longitudinal passage 56 that is subdivided into a proximal section 58 and a distal section 60 by a pair of longitudinally spaced internal grooves 62 and 64. The proximal section 58 is provided with an internal diameter that is slightly larger than the outer diameter of the proximal end 14 of the lead sleeve 13. The distal section 60 is provided with an internal diameter that is approximately the same size as the external diameter of the proximal O-ring 37 of the insulating jacket 36. The distal section 60 terminates in a proximally facing annular shoulder 66 against which the O-ring 39 is abutted when the connector 16 is fully inserted into the header 22. At the distal end of the distal section 62, an annular contact 68 is molded into the header 22. The annular contact 68 is connected to circuitry (not shown) housed in the can 30 via a conductor 70. The electrical contact 68 is provided with an internal diameter that is just slightly larger than the outer diameter of the pin 38 so that a good electrical contact is established when the pin 38 is inserted into the electrical contact 68.

The internal grooves 62 and 64 are provided with an inner diameter that is slightly smaller than the outer diameter of the annular seals 26 and 28 when those seals 26 and 28 are in the permanent shape shown in FIGS. 2 and 8. Prior to insertion of the lead connector 16 into the header 22, the annular seals 26 and 28 are deformed into the temporary shape shown in FIGS. 5 and 7. This deformation reduces the effective outer diameter of the annular seals 26 and 28 so that the connector 16 may be easily passed through the proximal section 58 of the longitudinal passage 56 in the header 22. The deformation of the seals 26 and 28 from their permanent shapes shown in FIGS. 2 and 8 to their temporary shapes shown in FIGS. 5 and 7 may be accomplished by heating the seals 26 and 28 above $T_g$ and deforming or bending the outer rims 52 and 53 toward the jacket 36 to establish the shapes with the outer diameter $D_2$. The heating may be by heated air, fluid bath or like method. If heat sterilization is used to sterilize the lead 10 prior to packaging, the deformation step may be combined with the sterilization process.

Following initial insertion into the proximal section 58, the lead connector 16 is advanced axially until the annular seals 26 and 28 are aligned with the internal grooves 62 and 64. This axial position relative to the header 22 also corresponds to the point at which the O-ring 39 abuts the annular shoulder 66 of the header structure 22. The annular seals 26 and 28 are then heated above their particular glass transition temperature, $T_g$. When the annular seals 26 and 28 are warmed above the glass transition temperature $T_g$, they return to the permanent shape shown in FIGS. 2 and 8 and thus fill into the internal grooves 62 and 64 to provide a secure seal against the passage of body fluids past the annular seals 26 and 28 and into the distal section 60 of the longitudinal passage 56.

Figure 9:
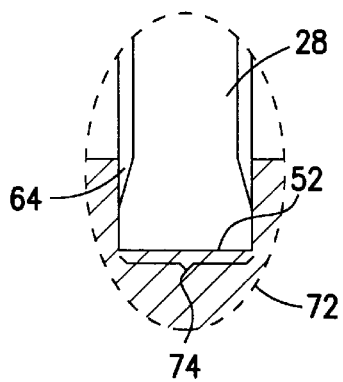
FIG. 9 is a magnified detailed view of a portion of the annular seal shown in FIG. 7.

The engagement between the annular seal 28 and the internal groove 64 may be understood by referring now also to FIG. 9, which is a detailed view of the portion shown in FIG. 8 circumscribed generally by the dashed oval 72. As shown in FIG. 8, the expansion of the annular seal 28 to the permanent shape shown in FIG. 8 brings the outer rim 52 of the annular seal 28 into snug, but compliant contact with the surface of the internal groove 64 to provide a fluid seal along the interface designated generally at 74 between the outer rim 52 and the bottom and the sidewalls of the groove 64.

It is desirable to heat and deform the seals 26 and 28 from their temporary shapes to their permanent shapes in situ. This may be accomplished by heating the header 22 until sufficient heat is transferred from the header 22 to the annular seals 28 and 28 to raise their temperature above $T_g$. The heating step will normally be conducted following implantation of the lead 10 but prior to placement of the cardiac stimulator 24 into the patient's tissue pocket. The heating may be advantageously conducted by forced air convection, such as via a hand held air blower, or other suitable heating method. It is desirable for the method used to heat the header 22 to avoid the potential for contamination of the longitudinal passage 56.

Figure 10:
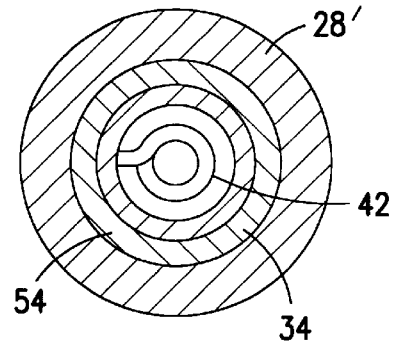
FIG. 10 is a cross-sectional view like FIG. 4 of an alternate exemplary embodiment of an annular seal in accordance with the present invention.

FIG. 10 is a cross-sectional view showing the same general perspective as FIG. 4, but depicts an alternate exemplary embodiment of the annular seal, now designated 28'. In this embodiment, the annular seal 28' and the segment 54 of the insulating jacket 36 are fabricated as separate structures. The annular seal 28' is positioned around the segment 54 and secured thereto by application of a suitable biocompatible adhesive of the types described generally above. Here, the segment 54 as well as the other portions of the insulating jacket 36 are molded around the chassis 34 and the conductor wire 42 is connected to the chassis 34 as generally described above. The annular seal 28' is advantageously composed of a thermally sensitive shape memory polymeric material and is deformable as generally described above.

Figure 11:
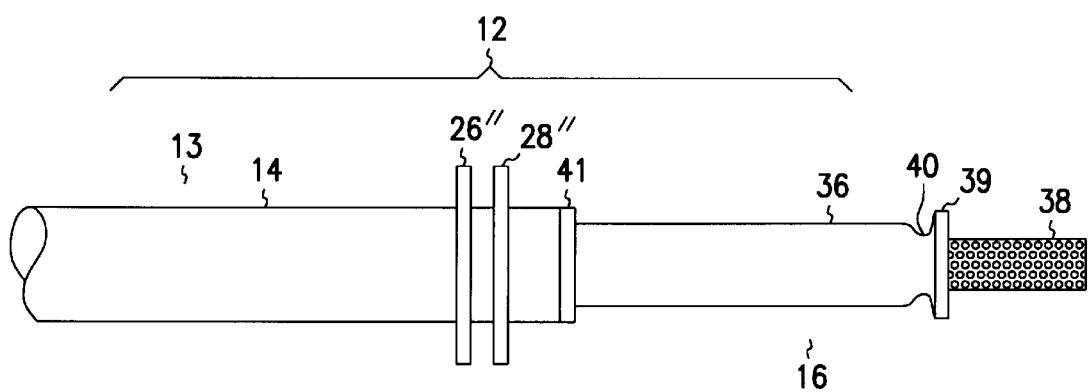
FIG. 11 is a detailed side view like FIG. 2 depicting an alternate exemplary embodiment of the cardiac lead in accordance with the present invention.

In the foregoing illustrative embodiments, the annular seals 26 and 28 and 28' are coupled to the insulating jacket 36 of the lead connector 16. However, the skilled artisan will appreciate that the seals may be coupled to the lead body 12 at a myriad of locations. For example and as shown in FIG. 11, the annular seals, now designated 26" and 28" may be integrally molded with the proximal end 14 of the lead sleeve 13. The annular seals 26" and 28" may be integrally molded with the lead sleeve 13 as shown or may be fabricated as separate structures and secured to the lead sleeve 13 via a biocompatible adhesive as shown generally in FIG. 10.

As noted above, the precise positioning of the annular seals 26" and 28" as well as the seals 26, 28, and 28' in the aforementioned embodiments is largely a matter of design discretion. Similarly, the skilled artisan will appreciate that the number of seals is also largely a matter of design discretion. For example, a single seal, such as the seal 28 may be used in lieu of multiple seals.

Figure 12:
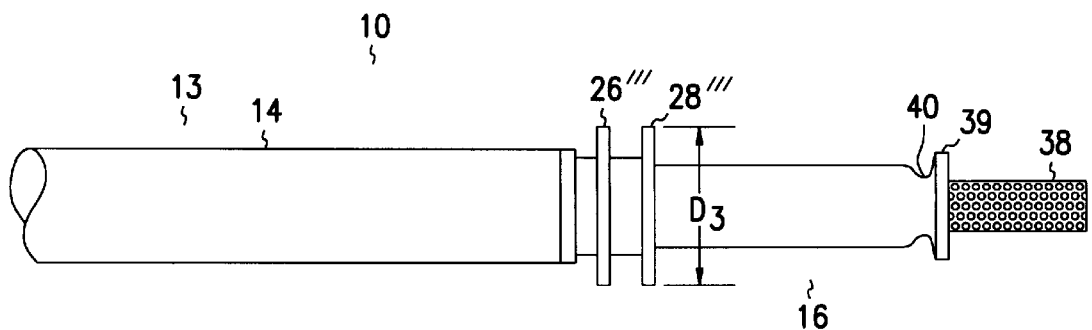
FIG. 12 is a detailed side view like FIG. 2 of another alternate embodiment of the cardiac lead in accordance with the present invention.
Figure 13:
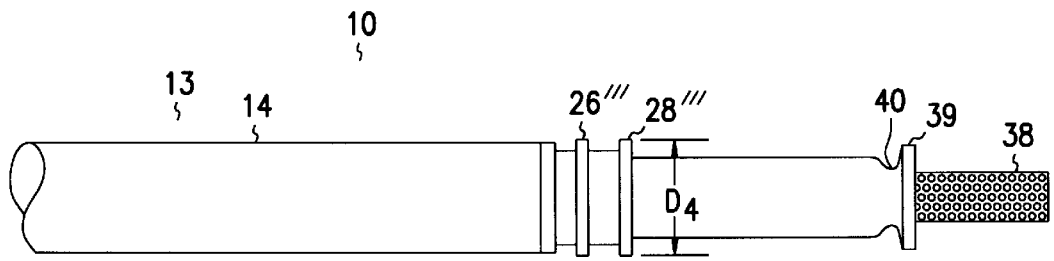
FIG. 13 is a detailed side view like FIG. 11 but depicting two annular seals deformed to a temporary shape prior to implantation in accordance with the present invention.

In the foregoing illustrated embodiments, the annular seals 26 and 28 are folded back into the temporary shape shown in FIG. 5 prior to insertion into the cardiac stimulator 24. However, other temporary shapes may be used that achieve the same design goals, that is, the deformation of an annular seal into a temporary shape that facilitates insertion into the cardiac stimulator header 22 and subsequent in situ deformation of the annular seal into a larger outer diameter that provides a secure fluid seal. For example, as shown in FIGS. 12 and 13, the annular seals, now designated 26''' and 28''', may be fabricated with a permanent diameter $D_3$ that is designed to provide a secure seal with the header 22 of the cardiac stimulator 24 shown in FIG. 1. Prior to insertion into the cardiac stimulator 24, the annular seals 26''' and 28''' are heated above their respective glass transition temperature $T_g$ and swaged or otherwise compressed to a outer diameter $D_4$, where $D_4<D_3$. Following insertion into the header 22 shown in FIG. 1, the header 22 may be heated as described above to deform the annular seals 26''' and 28''' to the larger outer diameter $D_3$ that is shown in FIG. 11.

Figure 14:
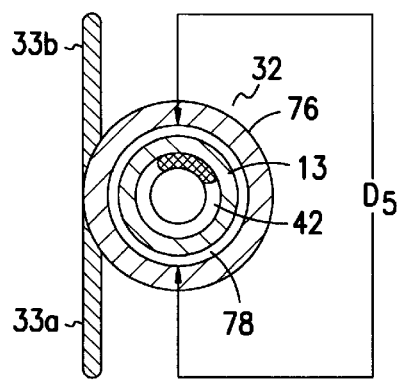
FIG. 14 is a cross-sectional view of FIG. 1 taken at section 14—14.
Figure 15:
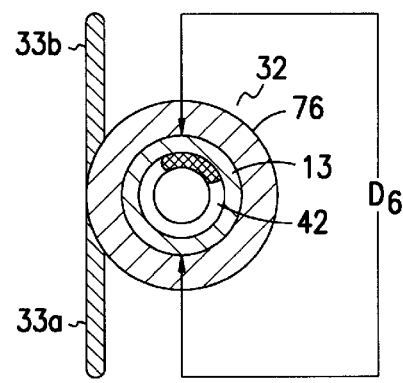
FIG. 15 is a cross-sectional view like FIG. 13 following deformation of the suture sleeve to a permanent shape in accordance with the present invention.

The detailed structure of the suture sleeve 32 may be understood by referring now to FIG. 1 and to FIG. 14, which is a cross-sectional view of FIG. 1 taken at section 14—14. The suture sleeve includes a tubular body 76 with a lumen 78 extending therethrough. Like the annular seals 26 and 28, the suture sleeve 32 is advantageously composed of a thermally-sensitive shape-memory polymeric material of the types described above. FIG. 14 shows the suture sleeve 32 deformed to a temporary shape with an inner diameter $D_5$. The deformation is such that the inner diameter $D_5$ is large enough to permit the suture sleeve 32 to be readily moved axially on the lead sleeve 13. Easy sliding of the suture sleeve 32 prior to implantation is desirable so that the implanting physician may position the suture sleeve to the desired tissue location for suturing, quickly and with minimal exertion. FIG. 15 is a cross-sectional view of the suture sleeve 32 like FIG. 14, but depicts the suture sleeve 32 following deformation to the permanent shape, that is, the shape in which the suture sleeve 32 is initially molded. Note that the suture sleeve 32 is initially molded with the permanent shape such that the inner diameter $D_6$ of the suture sleeve 32 is slightly smaller than the nominal outer diameter of the lead sleeve 13. In this way, when the suture sleeve 32 is heated above its glass transition temperature $T_g$, the suture sleeve 32 deforms from the temporary shape shown in FIG. 13 with an inner diameter $D_5$ to the permanent shape shown in FIG. 14 with an inner diameter $D_6$, and thereby establishes a snug interference fit with the exterior of the lead sleeve 13.

Following placement of the lead, the suture sleeve 32 is positioned at the site where suturing to tissue will occur. The suture sleeve 32 may be sutured in place prior to deformation to the permanent shape shown in FIG. 15 or after as desired. The heating may be by forced air convection, saline bath or like methods.

In contrast to conventional suture sleeves where reliance is placed on one or more longitudinally spaced sutures to prevent relative sliding movement between a suture sleeve and a lead sleeve, the suture sleeve 32 of the present invention provides an interference fit along the entire length of the interface between the lead sleeve 13 and the suture sleeve 32. The result is a secure engagement that distributes force evenly over the surface of the lead sleeve 13 and is not prone to loosen over time as a result of ligature material stretching and ligature knot failure.

Figure 16:
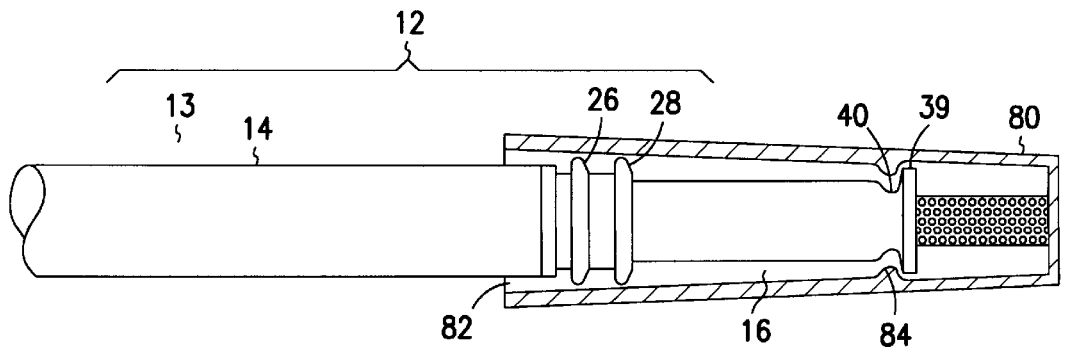
FIG. 16 is a detailed side view like FIG. 5 depicting placement of a protective cap over the portion of the lead body including the annular seal in accordance with the present invention.

It is desirable to protect the seals, such as the seals 26 and 28 shown in FIG. 5, prior to implantation. In this regard and as shown in FIG. 16, a protective cap 80 may be placed over the portion of the lead body 12 to which the seals 26 and 28 are coupled. The cap 80 includes a bore 82 that is of sufficient length to receive enough of the lead body 12 to cover and protect the seals 26 and 28. The cap 80 may be provided with a radially inwardly projecting annular rim 84 that snaps into the groove 39 to retain the cap 80 on the lead body 12. The cap 80 may be fabricated from a variety of materials. Biocompatibility is not necessary, although the capacity to withstand sterilization is desired.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac stimulator lead, comprising:

a lead body having a connector for coupling to a cardiac stimulator and a flexible insulating sleeve having a first outer diameter;

an electrode coupled to the insulating sleeve;

a conductor wire coupled between the connector and the electrode; and an annular seal coupled to the lead body and being composed of a thermally-sensitive shape-memory polymeric material whereby the seal is deformable in situ from a temporary shape with a second outer diameter to a permanent shape with a third outer diameter that is greater than the second outer diameter.

2. The cardiac stimulator lead of claim 1, wherein the annular seal has an outer rim, the outer rim being folded toward the lead body prior to deformation to the permanent shape and folded away from the lead body after deformation to the permanent shape.

3. The cardiac stimulator lead of claim 1, wherein the annular seal is coupled to the connector.

4. The cardiac stimulator lead of claim 1, wherein the annular seal is coupled to the insulating sleeve.

5. The cardiac stimulator lead of claim comprising a suture sleeve positioned around the insulating sleeve and being composed of a thermally-sensitive shape-memory polymeric material whereby the suture sleeve is deformable in situ from a temporary shape with a first inner diameter to a permanent shape with a second inner diameter that is less than than the first inner diameter and the first outer diameter of the insulating sleeve.

6. The cardiac stimulator lead of claim 1, comprising a cardiac stimulator for coupling to the connector.

7. The cardiac stimulator lead of claim 1, wherein the conductor wire comprises a conductor and an insulating jacket coating the conductor.

8. The cardiac stimulator lead of claim 1, wherein the thermally-sensitive shape-memory polymeric material comprises polynorbornene.

9. The cardiac stimulator lead of claim 1, comprising a cap removably coupled to the lead body, the cap including a bore of sufficient length to receive and cover the portion of the lead body having the annular seal.

10. A suture sleeve for a cardiac lead that has an insulating sleeve with a first outer diameter, comprising:

a tubular body having a lumen extending therethrough whereby the tubular body may be slipped over the cardiac lead, the tubular body being composed of a thermally-sensitive shape-memory polymeric material whereby the tubular body is deformable in situ from a temporary shape with a first inner diameter to a permanent shape with a second inner diameter that is less than the first inner diameter and the first outer diameter of the insulating sleeve.

11. The suture sleeve of claim 10, comprising first and second suture wings.

12. The suture sleeve of claim 10, wherein the thermally-sensitive shape-memory polymeric material comprises polynorbornene.

13. A cardiac stimulator lead, comprising:

a tubular lead body having a connector for connecting to a cardiac stimulator and an insulating sleeve coupled to the connector and having a first outer diameter;

an electrode coupled to the insulating sleeve;

a conductor wire coupled between the connector and the electrode; and a suture sleeve having a lumen extending therethrough to receive the insulating sleeve, the suture sleeve being composed of a thermally-sensitive shape-memory polymeric material whereby the suture sleeve is deformable in situ from a temporary shape with a first inner diameter to a permanent shape with a second inner diameter that is less than the first inner diameter and the first outer diameter of the insulating sleeve.

14. The cardiac stimulator lead of claim 13, comprising a cardiac stimulator for coupling to the connector.

15. The cardiac stimulator lead of claim 13, wherein the conductor wire comprises a conductor and an insulating jacket coating the conductor.

16. The cardiac stimulator lead of claim 13, wherein the thermally-sensitive shape-memory polymeric material comprises polynorbornene.

17. The cardiac stimulator lead of claim 13, wherein the suture sleeve includes first and second suture wings.

18. The cardiac stimulator lead of claim 13, comprising a cap removably coupled to the lead body, the cap including a bore of sufficient length to receive and cover the portion of the lead body having the annular seal.

* * * * *

UNITED STATES PATENT AND TRADEMARK OFFICE
CERTIFICATE OF CORRECTION

PATENT NO.: 6,002,969
DATED: December 14, 1999
INVENTOR(S): James E. Machek et al.

It is certified that error appears in the above-identified patent and that said Letters Patent is hereby corrected as shown below:

In the Abstract, line 6, please delete "seat" and insert --seal-- therefor.

In column 10, line 26, after "Claim", please insert --1-- therefor.

In column 10, line 33, please delete "than" after "than".

Signed and Sealed this

Fifth Day of December, 2000

Attest:

Q. TODD DICKINSON

Attesting Officer

Director of Patents and Trademarks